United States Patent
Bradley et al.

(10) Patent No.: US 10,537,741 B2
(45) Date of Patent: Jan. 21, 2020

(54) SYSTEM AND METHOD FOR CHOOSING ELECTRODES IN AN IMPLANTED STIMULATOR DEVICE

(75) Inventors: Kerry Bradley, Glendale, CA (US); Ljubomir Manola, Enschede (NL); Jan Holsheimer, Oldenzaal (NL)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 2734 days.

(21) Appl. No.: 11/295,168

(22) Filed: Dec. 5, 2005

(65) Prior Publication Data

US 2006/0195159 A1    Aug. 31, 2006

Related U.S. Application Data

(60) Provisional application No. 60/633,353, filed on Dec. 3, 2004.

(51) Int. Cl.
*A61N 1/36* (2006.01)

(52) U.S. Cl.
CPC ..... *A61N 1/36135* (2013.01); *A61N 1/36132* (2013.01); *A61N 1/36185* (2013.01)

(58) Field of Classification Search
CPC .............. A61N 1/36071; A61N 1/0551; A61N 1/36135
USPC .............................. 607/9, 17, 46, 48, 59, 62
See application file for complete search history.

(56) References Cited

U.S. PATENT DOCUMENTS

| | | | |
|---|---|---|---|
| 3,646,940 A | 3/1972 | Timm et al. | 128/421 |
| 3,724,467 A | 4/1973 | Avery et al. | 128/418 |
| 3,822,708 A | 7/1974 | Zilber | 128/419 R |
| 5,626,629 A * | 5/1997 | Faltys | A61N 1/36032 607/57 |
| 5,702,429 A | 12/1997 | King | 607/46 |
| 5,814,092 A | 9/1998 | King | 607/46 |
| 5,913,882 A | 6/1999 | King | 607/62 |
| 6,007,532 A * | 12/1999 | Netherly | A61B 5/0424 606/32 |

(Continued)

OTHER PUBLICATIONS

Publication No. IPCOM000021845D, published at www.ip.com (Feb. 12, 2004).

*Primary Examiner* — Michael J D Abreu
(74) *Attorney, Agent, or Firm* — Lowe Graham Jones PLLC; Bruce E. Black

(57) ABSTRACT

A method of selecting a subset of electrodes in a stimulator device implanted in a patient for further clinical evaluation is disclosed. The method comprises measuring at least first and second measurement for each of the plurality of electrodes that are indicative of the ability of the electrode if activated to provide useful therapy to the patient in which the stimulator device is implanted A weight is then determined for each of the measurements. The weight is then applied to each electrode measurement, which measurement may be normalized, and the weighted measurements for each electrode are preferably summed to arrive at a value which itself is indicative of a particular electrode's ability to provide useful therapy to the patient. These values can then be used to determine a subset of the electrodes useful for further clinical evaluation in the patient, which improved the accuracy and speeding determining appropriate patient therapy.

22 Claims, 13 Drawing Sheets

(56) References Cited

U.S. PATENT DOCUMENTS

| | | |
|---|---|---|
| 6,027,456 A | 2/2000 | Feler et al. .................... 600/554 |
| 6,175,767 B1* | 1/2001 | Doyle, Sr. ....................... 607/57 |
| 6,181,969 B1 | 1/2001 | Gord ............................... 607/59 |
| 6,516,227 B1 | 2/2003 | Meadows et al. .............. 607/46 |
| 6,609,029 B1 | 8/2003 | Mann et al. |
| 6,741,892 B1 | 5/2004 | Meadows et al. |
| 7,519,428 B1* | 4/2009 | Palmer ........................... 607/57 |
| 2003/0088189 A1* | 5/2003 | Tu ........................... A61B 5/053 |
| | | 600/549 |
| 2003/0139781 A1* | 7/2003 | Bradley ................... A61N 1/08 |
| | | 607/48 |
| 2004/0116978 A1 | 6/2004 | Bradley .......................... 607/48 |
| 2005/0182447 A1* | 8/2005 | Schecter ............. A61N 1/3627 |
| | | 607/2 |
| 2006/0095092 A1* | 5/2006 | Drew ............................. 607/60 |

\* cited by examiner

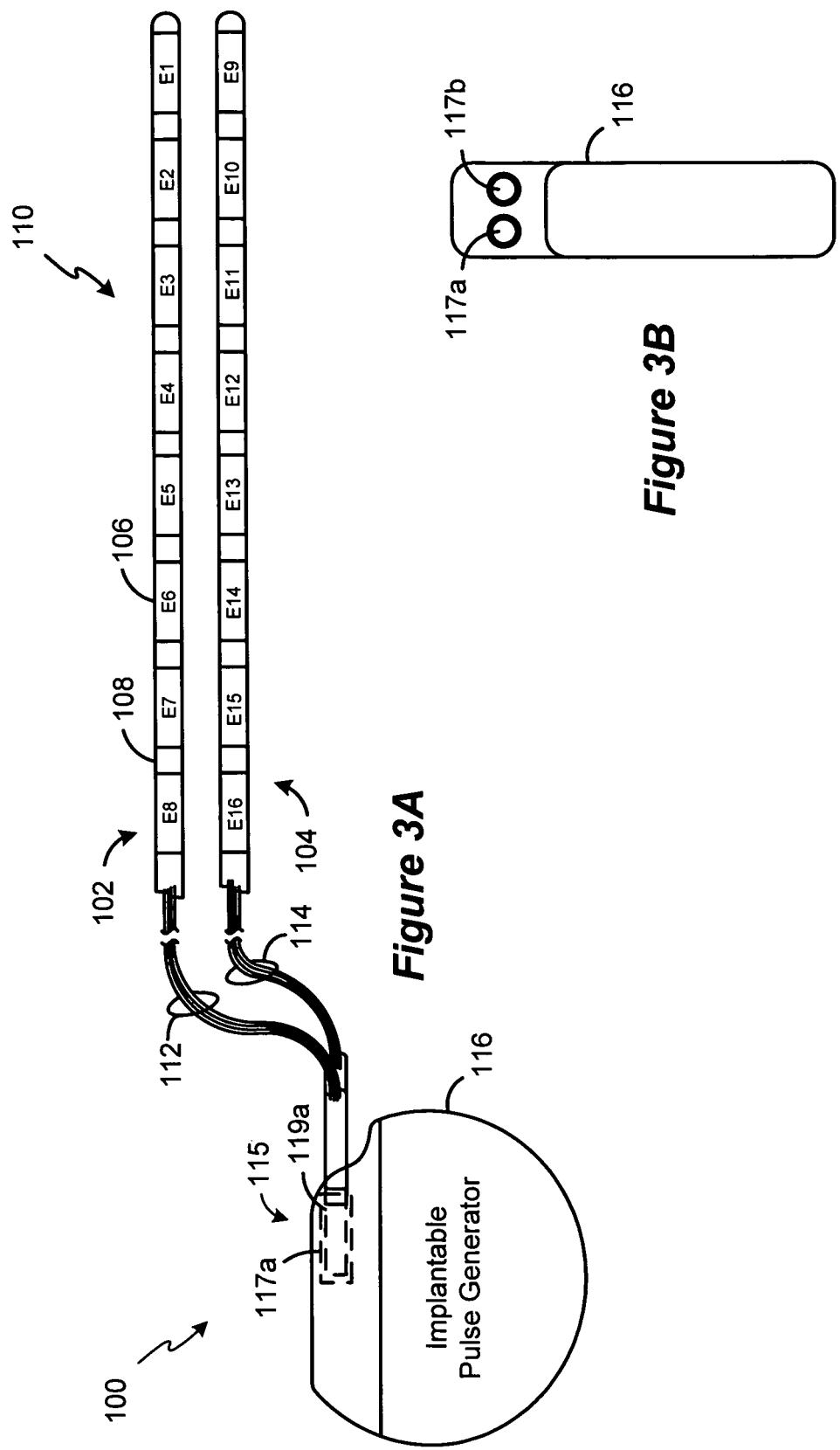
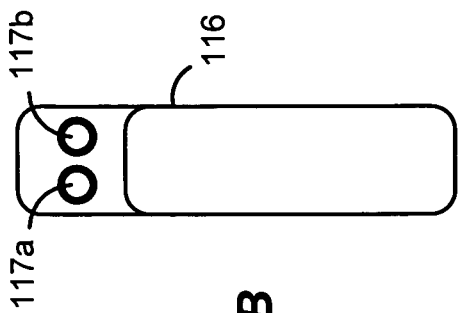
Figure 3A
Figure 3B

| | E₁ | E₂ | E₃ | E₄ | E₅ | E₆ | E₇ | E₈ | STD | AVG | STD/AVG (rank) | weight |
|---|---|---|---|---|---|---|---|---|---|---|---|---|
| Impedance (ohms) | 5K | 4K | 300 | 200 | 300 | 500 | 6K | 7K | 2.9K | 2.9K | 0.99 (1) | 40% |
| 1/Field Potential (1/Volts) | 0.20 | 0.18 | 0.18 | 0.17 | 0.17 | 0.17 | 0.22 | 0.22 | 0.024 | 0.19 | 0.13 (4) | 10% |
| Nerve Response (current, mA) | 5.0 | 4.0 | 4.0 | 4.0 | 3.0 | 4.0 | 4.0 | 8.0 | 1.51 | 4.5 | 0.33 (3) | 20% |
| User Input (scale of 1 (good) 10 bad) | 4 | 5 | 3 | 6 | 3 | 7 | 7 | 9 | 2.13 | 5.5 | 0.39 (2) | 30% |

Impedance, 1/Field Potential, Nerve Response: objective
User Input: subjective

*Figure 10A*

|  | $E_1$ | $E_2$ | $E_3$ | $E_4$ | $E_5$ | $E_6$ | $E_7$ | $E_8$ |
|---|---|---|---|---|---|---|---|---|
| Normalized Impedance (/AVG) | 1.72 | 1.37 | 0.10 | 0.07 | 0.10 | 0.17 | 2.06 | 2.40 |
| Normalized Field Potential (/AVG) | 1.06 | .096 | .096 | 0.88 | 0.88 | 0.88 | 1.18 | 1.18 |
| Normalized Nerve Response (/AVG) | 1.11 | 0.89 | 0.89 | 0.89 | 0.67 | 0.89 | 0.89 | 1.78 |
| User Input (/AVG) | 0.72 | 0.90 | 0.54 | 1.09 | 0.54 | 1.27 | 1.27 | 1.63 |

(first three rows: objective; last row: subjective)

*Figure 10B*

| | E₁ | E₂ | E₃ | E₄ | E₅ | E₆ | E₇ | E₈ |
|---|---|---|---|---|---|---|---|---|
| Normalized Impedance * weight | 0.68 | 0.55 | 0.04 | 0.03 | 0.04 | 0.07 | 0.82 | 0.96 |
| Normalized Field Potential * weight | 0.11 | 0.10 | 0.10 | 0.09 | 0.09 | 0.09 | 0.12 | 0.12 |
| Normalized Nerve Response * weight | 0.22 | 0.18 | 0.18 | 0.18 | 0.13 | 0.18 | 0.18 | 0.36 |
| Normalized User Input * weight | 0.22 | 0.27 | 0.16 | 0.33 | 0.16 | 0.38 | 0.38 | 0.49 |
| SUM (=Value(E_X)) | 1.23 | 1.10 | 0.47 | 0.62 | 0.42 | 0.71 | 1.50 | 1.93 | objective: Normalized Impedance, Normalized Field Potential, Normalized Nerve Response
subjective: Normalized User Input

*Figure 10C*

SYSTEM AND METHOD FOR CHOOSING ELECTRODES IN AN IMPLANTED STIMULATOR DEVICE

CROSS REFERENCE TO RELATED APPLICATIONS

This application is a non-provisional filing of U.S. Provisional Patent Application Ser. No. 60/633,353, filed Dec. 3, 2004, which is incorporated herein in its entirety and to which priority is claimed pursuant to 35 U.S.C. § 119(e).

FIELD OF THE INVENTION

The present invention relates to therapeutic electrical stimulation systems and methods and, more specifically, relates to activating electrodes in an implanted stimulator device.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a spinal cord stimulation system, such as that disclosed in U.S. Pat. No. 6,516,227 ("the '227 patent"), issued Feb. 4, 2003 in the name of inventors Paul Meadows et al., which is incorporated herein by reference in its entirety.

Spinal cord stimulation is a well-accepted clinical method for reducing pain in certain populations of patients. A Spinal Cord Stimulation (SCS) system typically includes an Implantable Pulse Generator (IPG) or Radio-Frequency (RF) transmitter and receiver, electrodes, at least one electrode lead, and, optionally, at least one electrode lead extension. The electrodes, which reside on a distal end of the electrode lead, are typically implanted along the dura of the spinal cord, and the IPG or RF transmitter generates electrical pulses that are delivered through the electrodes to the nerve fibers within the spinal column. Individual electrodes are arranged in a desired pattern and spacing to create an electrode array. Individual wires within one or more electrode leads connect with each electrode in the array. The electrode lead(s) exit the spinal column and generally attach to one or more electrode lead extensions. The electrode lead extensions, in turn, are typically tunneled around the torso of the patient to a subcutaneous pocket where the IPG or RF receiver is implanted. Alternatively, the electrode lead may directly connect with the EPG or RF receiver. For examples of other SCS systems and other stimulation system, see U.S. Pat. Nos. 3,646,940 and 3,822,708, which are hereby incorporated by reference in their entireties. Of course, implantable pulse generators are active devices requiring energy for operation, such as is provided by an implanted battery or an external power source.

There are several types of leads presently used in spinal cord stimulation. One type is a percutaneous lead, which can have electrodes linearly positioned on the distal portion of the lead. A conventional lead implantation procedure commonly places the linearly positioned electrode array parallel to the spinal cord column at or near the physiological mid-line. Precise placement of the electrodes relative to the target nerves is critical for achieving a satisfactory physiological response to electrical stimulation and for keeping stimulation thresholds low in order to conserve battery power.

In addition to precise placement of the electrode array, proper selection of the electrodes, i.e., which of the electrodes in the array should be active in a given patient, is critical for achieving effective stimulation therapy. However, because of the uncertainties of the distances of the electrodes from the neural target, the unknown nature of the specific conductive environment in which the electrode is placed, etc., it generally cannot be known in advance and with precision which combination of active electrodes will be perceived by a patient as providing optimal therapy. As a result, patient therapy generally requires at the outset that various electrode combinations be tried and feedback received from the patient as to which of the combinations feels most effective from a quantitative and qualitative standpoint. When one considers that the electrodes can be operated in many different modes (e.g., monopolar, bipolar, multipolar) and that a given electrode can operate as a current source or sink with variable relative current amplitudes, pulse durations, and pulse frequencies, it turns out that there can be many electrode combinations that might need to be tried on a given patient.

Therefore, it can be a difficult and time-consuming task to try every single electrode combination on a given patient, and trying all such combinations might not be possible in a given clinical setting, which at best may last for a few hours. As a result, because only a relatively small number of combinations can be tested, the results can be haphazard and can provide imperfect results because the best active electrode combinations to deal with the patient's chronic pain may be missed.

Accordingly, what is needed is a method of intelligently selecting the possible active electrode combinations to improve the accuracy and speed of this process.

SUMMARY

A method of selecting of subset of electrodes in a stimulator device implanted in a patient for further clinical evaluation is disclosed. In one embodiment, the method comprises measuring at least first and second measurement for each of the plurality of electrodes that are indicative of the ability of the electrode if activated to provide useful therapy to the patient in which the stimulator device is implanted, such as electrode impedance, field potential, and nerve response. The measurements can be objective such as those measurements just mentioned, or can comprise subjective measurements which are quantified in response to qualitative feedback from the patient. A weight is then determined for each of the measurements, which may be a predetermined weight or determined on the basis of the variance of the measurement between the electrodes. The weight is then applied to each electrode measurement, which measurement may be normalized, and the weighted measurements for each electrode are preferably summed to arrive at a value which itself is indicative of a particular electrode's ability to provide useful therapy to the patient.

Once this subset of electrodes are determined, then clinical testing can be performed in a more simple and rapid fashion. Reducing the number of electrodes to be considered for therapy exponentially reduces the number of electrode combinations that are possible, and thus decreases the amount of time needed for setting optimal stimulation parameters (such as pulse width, pulse amplitude, and pulse rate) for a given patient.

BRIEF DESCRIPTION OF THE DRAWINGS

The above and other aspects of the present invention will be more apparent from the following more particular description thereof, presented in conjunction with the following drawings, in which:

FIGS. 3A and 3B show the electrode array and the manner in which it is coupled to the implantable stimulator device in the SCS system of FIGS. 1 and 2.

FIGS. 10A-10C show examples of the various per-electrode objective and/or subjective measurements that can be taken, and how those measurements can be normalized and weighted to arrive at a subset of electrodes optimal for further clinical examination in a given patient.

Corresponding reference characters indicate corresponding components throughout the several views of the drawings.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims and their equivalents.

Before discussing schemes for the selection of active electrodes that are the focus of this disclosure, the circuitry, structure, and function of an implantable stimulator device in which the technique can be used is set forth for completeness.

The disclosed implantable stimulator device may comprise an implantable pulse generator (IPG) or similar electrical stimulator and/or electrical sensor that may be used as a component of numerous different types of stimulation systems. More specifically, the description that follows relates to use of the invention within a spinal cord stimulation (SCS) system as an exemplary embodiment. However, it is to be understood that the invention is not so limited. Rather, the invention may be used with any type of implantable electrical circuitry that could benefit from the disclosed technique. For example, the present invention may be used as part of a pacemaker, an implantable pump, a defibrillator, a cochlear stimulator, a retinal stimulator, a stimulator configured to produce coordinated limb movement, a cortical or deep brain stimulator, or in any other stimulator configured to treat urinary incontinence, sleep apnea, shoulder sublaxation, etc. Moreover, the technique can be used in non-medical and/or non-implantable devices or systems as well.

Figure 1:
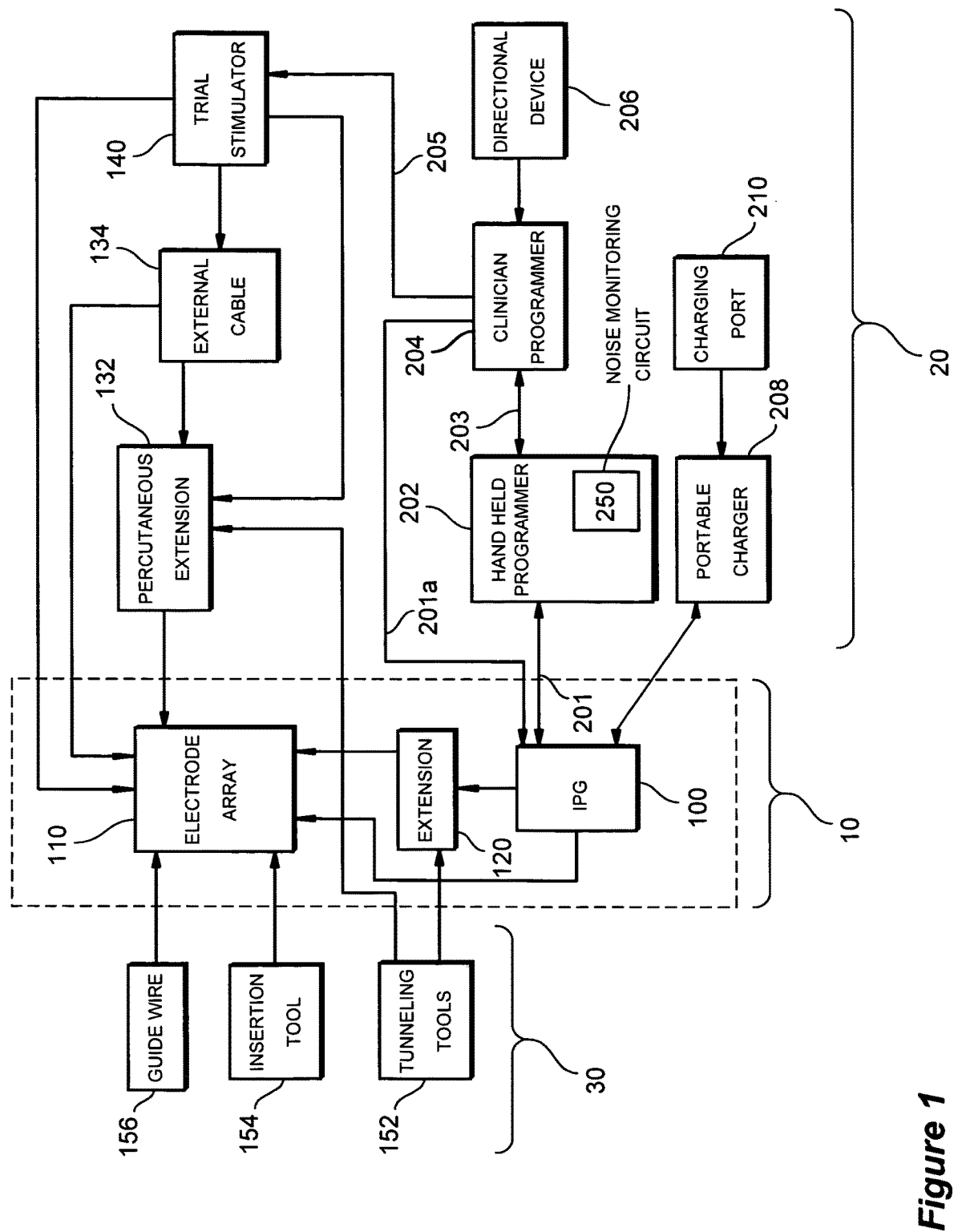
FIG. 1 shows a block diagram that illustrates exemplary implantable, external, and surgical components of a spinal cord stimulation (SCS) system that employs an implantable stimulator device in accordance with the present invention.

Turning first to FIG. 1, a block diagram is shown that illustrates the various components of an exemplary SCS system in which the invention may be used. These components may be subdivided into three broad categories: implantable components 10, external components 20, and surgical components 30. As seen in FIG. 1, the implantable components 10 include an implantable pulse generator (IPG) 100, an electrode array 110, and (as needed) a lead extension 120. The extension 120 may be used to electrically connect the electrode array 110 to the IPG 100. In an exemplary embodiment, the IPG 100, described more fully below, may comprise a rechargeable, multi-channel, telemetry-controlled, pulse generator housed in a rounded high-resistivity titanium alloy case 116 (FIG. 3A) to reduce eddy current heating during the inductive charging process. The IPG 100 may provide electrical stimulation through a multiplicity of electrodes, e.g., sixteen electrodes, included within the electrode array 110, as discussed further below with reference to FIGS. 3A and 3B.

Figure 4A:
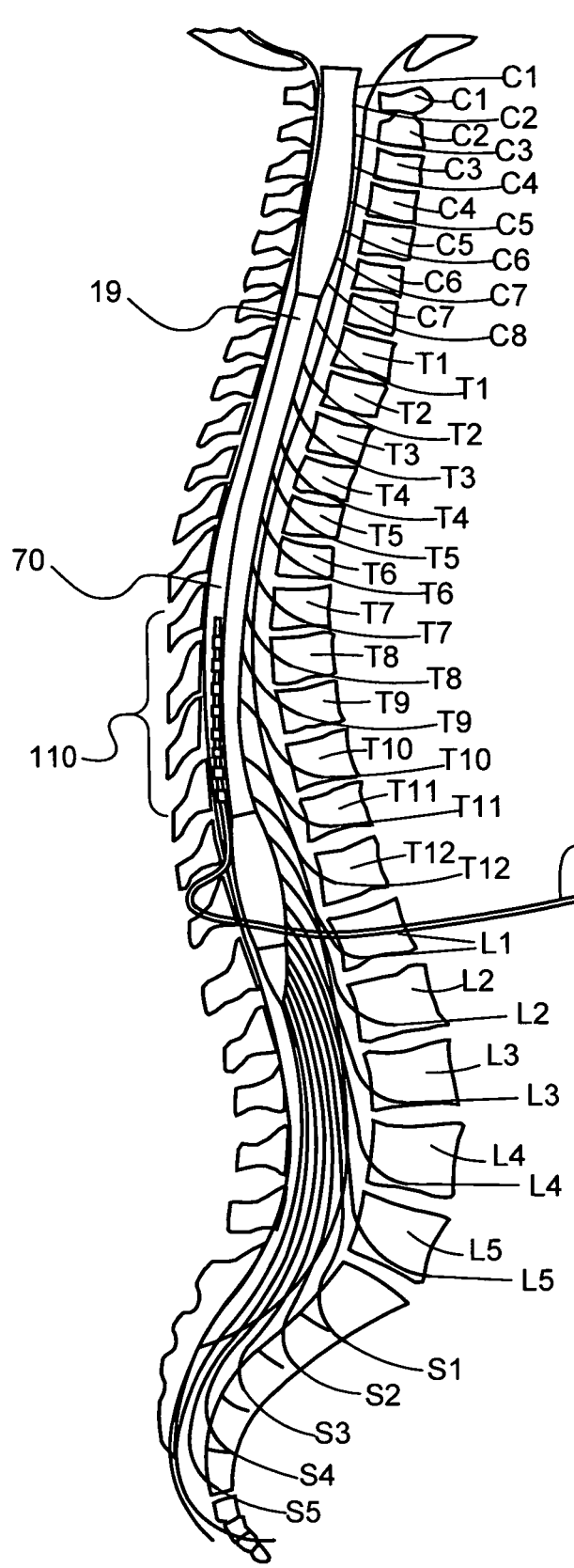
FIGS. 4A and 4B show a placement of the percutaneous lead for spinal cord stimulation with an in-line electrode array inserted alongside the spinal cord in the epidural space, in close proximity to the dura mater.
Figure 4A:
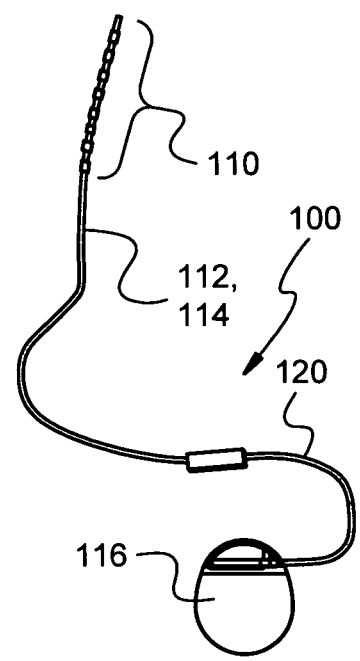
Figure 4B:
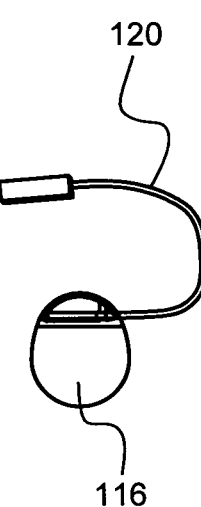

Typically, the IPG 100 is placed in a surgically-made pocket either in the abdomen, or just at the top of the buttocks. It may, of course, also be implanted in other locations of the patient's body. Once implanted, the IPG 100 is detachably connected to the lead system, comprising the lead extension 120, if needed, and the electrode array 110. The electrode array 110 and its various signal wires 112, 114 and/or extensions lead extension 120, for example, may be tunneled up to the spinal column, such as in the epidural space 70 next to the spinal cord 19, as shown in FIG. 4B. Once implanted and any trial stimulation period is complete, the electrode array 110 and lead extension 120 are intended to be permanent. In contrast, the IPG 100 may be replaced when its power source fails or for other reasons.

Figure 2:
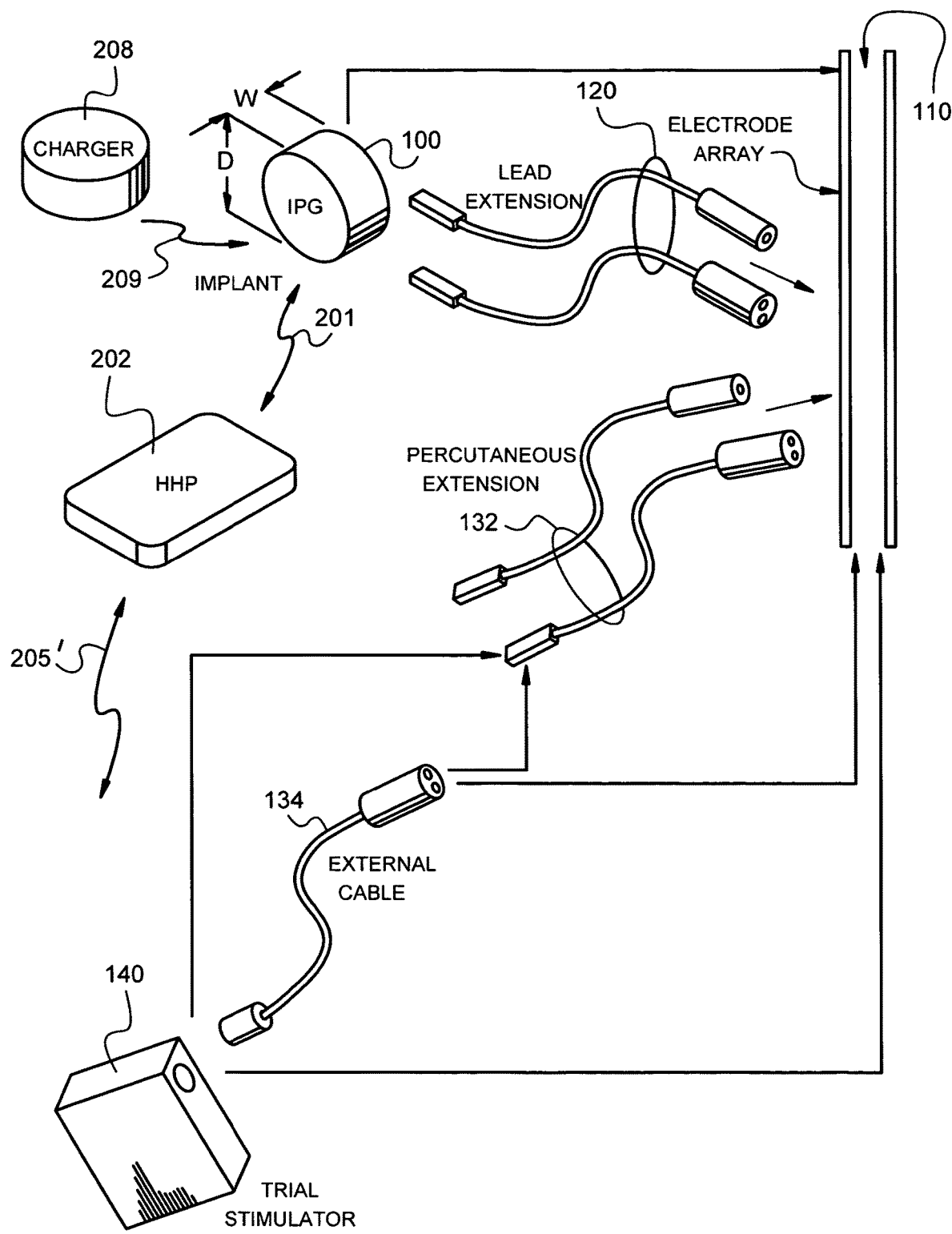
FIG. 2 shows various components of the SCS system of FIG. 1.

As seen best in FIG. 2, and as also illustrated in FIG. 1, the electrode array 110 and its associated lead system typically interface with the implantable pulse generator (IPG) 100 via the lead extension system 120 just mentioned. The electrode array 110 may also be connected to an external trial stimulator 140, through the use of a percutaneous lead extension 132 and/or an external cable 134. The external trial stimulator 140 typically includes the same or similar pulse generation circuitry as does the IPG 100, and is used on a trial basis, e.g., for 7-10 days, after the electrode array has been implanted and prior to implantation of the IPG 100, to test the effectiveness of the stimulation that is to be provided.

FIGS. 3A and 3B show the electrode array 110 and the manner in which it is coupled to the IPG 100. As shown, the electrode array 110 comprises first and second implantable leads 102 and 104. Leads 102 and 104 are in-line leads, meaning that both consist of a plurality of in-line electrodes 106. The electrodes are carried on a flexible body 108. In the illustrated embodiment, there are eight electrodes on lead 102, labeled $E_1$-$E_8$, and eight electrodes on lead 104, labeled $E_9$-$E_{16}$. The actual number of leads and electrodes will, of course, vary according to the intended application and should not be understood in any limiting sense. As discussed above, leads 102 and 104 may be implanted into a desired location, such as adjacent to the patient's spinal column, through the use of an insertion needle or other conventional techniques.

Each of the electrodes 106 on lead 102 are electrically connected to the IPG 100 by a first signal wire 112 that extends through, or is imbedded in, the associated flexible body 108. Similarly, each of the electrodes 106 on the lead 104 are electrically connected to the IPG 100 by second signal wires 114. The signal wires 112 and 114 and/or the lead extension 120 are connected to the IPG 100 by way of an interface 115. The interface 115 may be any suitable device that allows the leads 102 and 104 and/or lead extension 120 to be removably connected to the IPG 110. Interface 115 may comprise, for example, an electromechanical connector arrangement including lead connectors 117a and 117b (FIG. 3A) configured to mate with corresponding connectors (only connector 119a is shown) on the leads 102 and 104. Alternatively, the leads 102 and 104 can share a single connector that mates with a corresponding connector on the IPG 100. Exemplary connector arrangements are disclosed in U.S. Pat. Nos. 6,609,029 and 6,741,892, which are incorporated herein by reference. Although the electrode array is shown as having two in-line leads 102, 104 each with a plurality of electrodes 106 (e.g., 8 each), it should be understood that more or fewer leads could be used. For example, a single in-line lead with 16 linearly-arranged electrodes 106 could be used as well.

Referring again to FIGS. 1 and 2, and as noted earlier, a hand-held programmer (HHP) 202 may be used to control the IPG 100 via a suitable non-invasive communications link 201, e.g., an RF link. Such control allows the IPG 100 to be turned on or off, and generally allows stimulation parameters, e.g., pulse amplitude, width, and rate, to be set by a patient or clinician within prescribed limits. The HHP 202 may also be linked with the external trial stimulator 140 through another link 205', e.g., an infra red link. Detailed programming of the IPG 100 is preferably accomplished through the use of an external clinician's programmer (CP) 204 (FIG. 1), which may also be hand-held and which may be coupled to the IPG 100 directly via link 201a or indirectly through the HHP 202. An external charger 208, non-invasively coupled with the IPG 100 through link 209, e.g., an inductive link, allows energy stored or otherwise made available to the charger 208 to be coupled into the rechargeable battery housed within the IPG 100.

Figure 5:
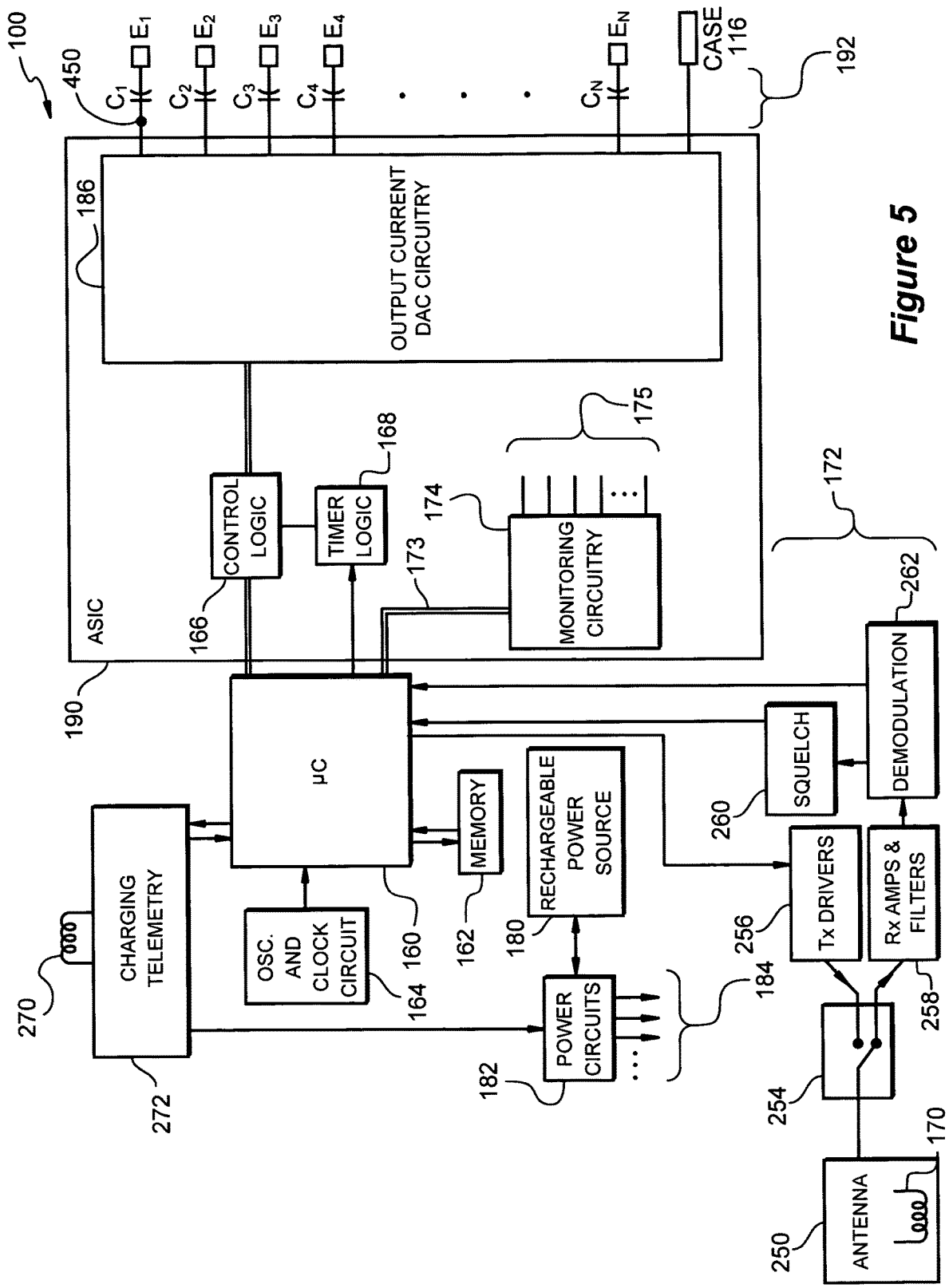
FIG. 5 shows a block diagram that illustrates the main components of one embodiment of an implantable stimulator device in which the invention can be used.

Turning next to FIG. 5, a block diagram is shown that illustrates the main components of one embodiment of an implantable pulse generator (IPG) 100 in which embodiments of the invention may be used. As seen in FIG. 5, the IPG includes a microcontroller (μC) 160 connected to memory circuitry 162. The μC 160 typically comprises a microprocessor and associated logic circuitry which in combination with control logic circuits 166, timer logic 168, and an oscillator and clock circuit 164, generate the necessary control and status signals to allow the μC 160 to control the operation of the IPG in accordance with a selected operating program and stimulation parameters.

The operating program and stimulation parameters are telemetered to the IPG 100, where they are received via antenna 250 (which may include a coil 170 and/or other antenna components), processed, e.g., via RF-telemetry circuitry 172, and may be stored, e.g., within the memory 162. The RF-telemetry circuitry 172 demodulates the signal it receives from the HHP 202 or CP 204 to recover the operating program and/or the stimulation parameters. More specifically, signals received by the antenna 250 are passed through the transmit/receive switch 254 to amplifiers and filters 258. From there, the received signals are demodulated (262) using Frequency Shift Keying (FSK) demodulation for example, and the data is then sent to the microcontroller 160 for processing and/or eventual storage. When RF-telemetry circuitry 172 is used to transmit information to the HHP 202 or CP 204 to report in some fashion on its status, the microcontroller 160 sends relevant data to transmission drivers 256, where the carrier is modulated by the data and amplified for transmission. The transmit/receive switch 254 would then be set to communicate with the transmission drivers 256, which in turn drive the data to the antenna 250 to be broadcast.

The microcontroller 160 is further coupled to monitoring circuits 174 via bus 173. The monitoring circuits 174 monitor the status of various nodes or other points 175 throughout the IPG 100, e.g., power supply voltages, current values, temperature, the impedance of electrodes attached to the various electrodes $E_1 \ldots E_N$, and the like. Informational data sensed through the monitoring circuit 174 may be sent to a remote location external to the IPG (e.g., a non-implanted location) through telemetry circuitry 172 via coil 170. Further details concerning the monitoring circuitry 174 will be discussed later in this disclosure.

The operating power for the IPG 100 may be derived from a rechargeable power source 180, which may comprise a lithium-ion or lithium-ion polymer battery, for example. The rechargeable battery 180 provides an unregulated voltage to power circuits 182. The power circuits 182, in turn, generate the various voltages 184, some of which are regulated and some of which are not, as needed by the various circuits located within the IPG 100. In a preferred embodiment, the battery 180 is charged by an electromagnetic field created by an external portable charger 208 (FIG. 1). When placed near the IPG 100 (e.g., centimeters away), an electromagnetic field emanating from the portable charger 208 induces a current in charging coil 270 (even through a patient's skin). This current is then rectified and regulated to charge the battery 180. Further associated with the charging circuitry is charging telemetry circuitry 272, which is used for example by the IPG 100 to report back to the portable charger 208 when the battery is full, and thus when portable charger can be shut off.

In one exemplary embodiment, any of the N electrodes may be assigned to up to k possible groups or "channels." In one preferred embodiment, k may equal four. Moreover, any of the N electrodes can operate, or be included in, any of the k channels. The channel identifies which electrodes are selected to synchronously source or sink current to create an electric field in the tissue to be stimulated. Amplitudes and polarities of electrodes on a channel may vary, e.g., as controlled by the HHP 202 and/or the CP 204.

Figure 7:
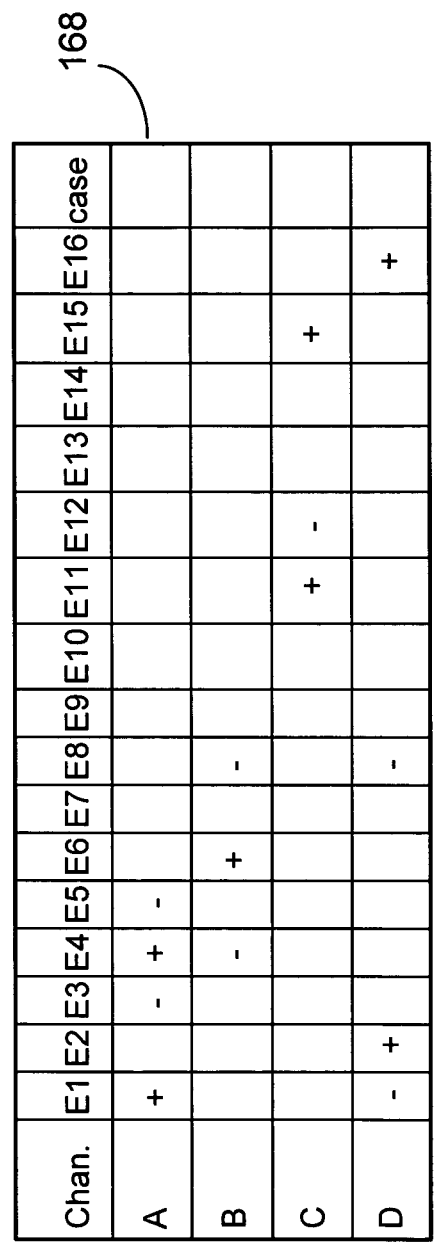
FIG. 7 shows an example of various timing channels usable in an implantable stimulator device, and shows whether each electrode in a channel operates as a source or sink of current.

For example, as shown in FIG. 7, four channels are defined, and represent groups of electrodes that will be activated as either sources or sinks at a particular time. Thus, in a first timing channel A, electrodes $E_1$ and $E_4$ will act as current sources (denoted by the plus symbol), while electrodes $E_3$ and $E_5$ will act as sinks (denoted by the minus symbol). Electrodes without any designator in FIG. 7 are not activated and do not participate in the sourcing or sinking of current. By designating different channels in this manner, the stimulation provided to the patient can be freely varied with desired therapeutic effect. Note that the case 116 (FIG. 3A) of the IPG 100 can also operate as an electrode which can source or sink current. This allows the IPG to be operated in any number of different modes, e.g., a monopolar mode (one electrode $E_X$ active with an active case), a bipolar mode (two electrodes $E_X$ active), or a multipolar mode (more than two electrodes $E_X$ active).

Ultimately, the grouping of the electrodes into different channels is managed by the control logic 166 (FIG. 5), with the timing of the activation of the various electrodes in each channel being handled by the timer logic 168. The control logic 166, receiving commands from the microcontroller 160, further sets the amplitude of the current pulse being sourced or sunk to or from a given electrode. Such current pulse may be programmed to one of several discrete current levels, e.g., between 0 to 10 mA in steps of 0.1 mA. The pulse width of the current pulses is preferably adjustable in convenient increments, e.g., from 0 to 1 milliseconds (ms) in increments of 10 microseconds (μs). Similarly, the pulse rate is preferably adjustable within acceptable limits, e.g., from 0 to 1000 Hz. Other programmable features can include slow start/end ramping, burst stimulation cycling (on for X time, off for Y time), and open or closed loop sensing modes.

The stimulation pulses generated by the IPG 100 may be charge balanced. This means that the amount of positive charge associated with a given stimulus pulse is offset with an equal and opposite negative charge. Charge balance may be achieved through coupling capacitors $C_X$, which provide a passive capacitor discharge that achieves the desired charge-balanced condition. Alternatively, active biphasic or multi-phasic pulses with positive and negative phases that are balanced may be used to achieve the needed charge balanced condition.

As shown in FIG. 5, much of circuitry included within the IPG 100 may be realized on a single application specific integrated circuit (ASIC) 190. This allows the overall size of the IPG 100 to be quite small, and readily housed within a suitable hermetically-sealed case 116 (FIG. 3A). The IPG 100 may include feedthroughs to allow electrical contact to be individually made from inside of the hermetically-sealed case with the N electrodes that form part of the lead system outside of the case, as was discussed above with reference to FIG. 3B.

The telemetry features of the IPG 100 allow the status of the IPG to be checked as noted earlier. For example, when the HHP 202 and/or the CP 204 initiate a programming session with the IPG 100 (FIG. 1), the capacity of the battery is telemetered so that the external programmer can calculate the estimated time to recharge. Any changes made to the current stimulus parameters are confirmed through back-telemetry, thereby assuring that such changes have been correctly received and implemented within the implant system. Moreover, upon interrogation by the external programmer, all programmable settings stored within the implant system 10 may be uploaded to one or more external programmers.

Figure 6:
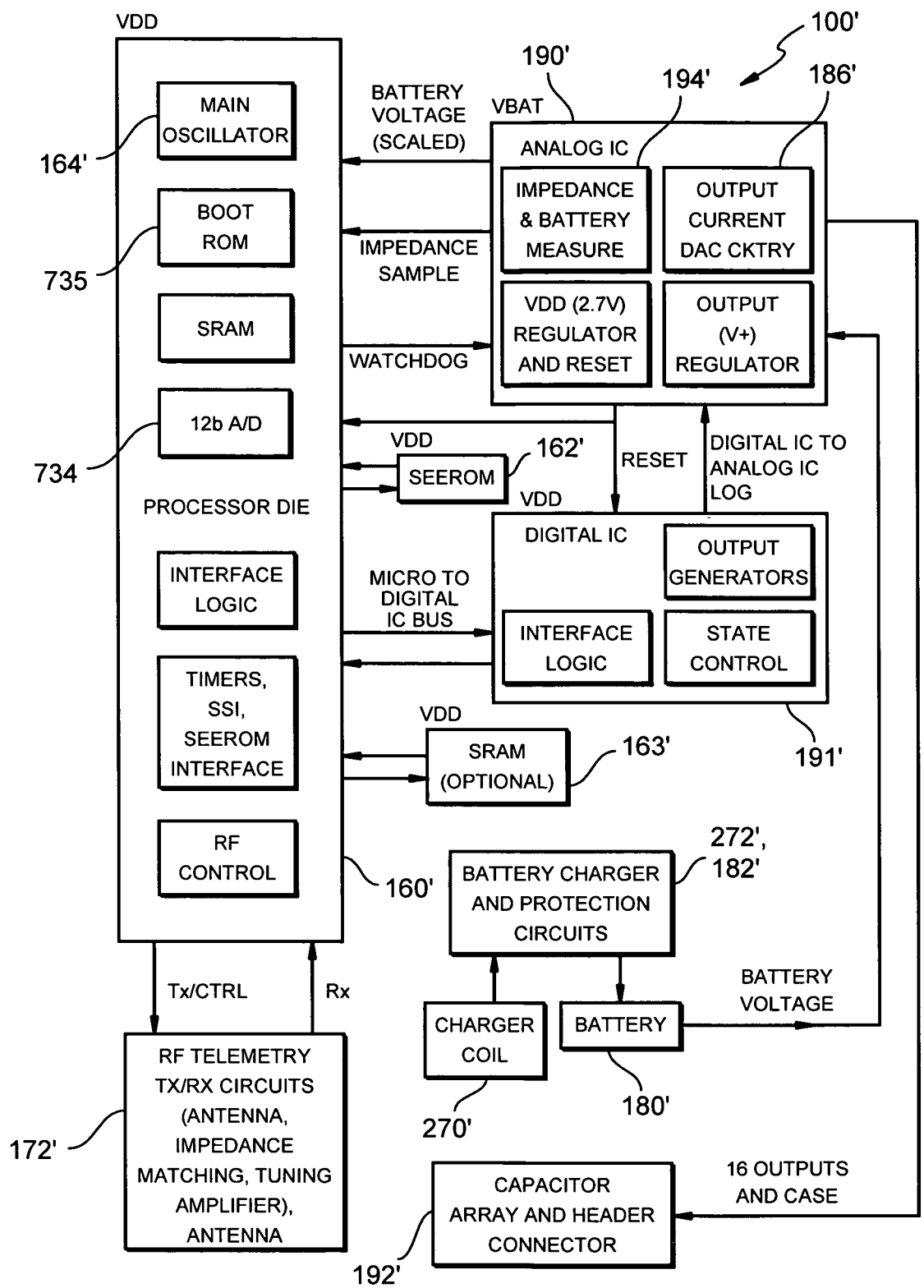
FIG. 6 shows a block diagram that illustrates another embodiment of an implantable stimulator device in which the invention can be used.

Turning next to FIG. 6, a hybrid block diagram of an alternative embodiment of an IPG 100' that may be used with the invention is illustrated. The IPG 100' includes both analog and digital dies, or integrated circuits (ICs), which may be housed in a single hermetically-sealed rounded case having, for instance, a diameter of about 45 mm and a maximum thickness of about 10 mm. Many of the circuits contained within the IPG 100' are identical or similar to the circuits contained within the IPG 100, shown in FIG. 5. The IPG 100' includes a processor die, or chip, 160', an RF telemetry circuit 172' (typically realized with discrete components), a charger coil 270', a rechargeable battery 180', battery charger and protection circuits 272', 182', memory circuits 162' (SEEPROM) and 163' (SRAM), a digital IC 191', an analog IC 190', and a capacitor array and header connector 192'.

The capacitor array and header connector 192' include sixteen output decoupling capacitors, as well as respective feed-through connectors for connecting one side of each decoupling capacitor through the hermetically-sealed case to a connector to which the electrode array 110, or lead extension 120, may be detachably connected.

The processor 160' may be realized with an application specific integrated circuit (ASIC), field programmable gate array (FPGA), or the like that comprises a main device for full bi-directional communication and programming. The processor 160' may utilize an 8086 core (the 8086 is a commercially-available microprocessor available from, e.g., Intel), or a low power equivalent thereof, SRAM or other memory, two synchronous serial interface circuits, a serial EEPROM interface, and a ROM boot loader 735. The processor die 160' may further include an efficient clock oscillator circuit 164', and (as noted earlier) mixer and modulator/demodulator circuitry implementing the QFAST RF telemetry method. An analog-to-digital converter (A/D) circuit 734 is also resident on the processor 160' to allow monitoring of various system level analog signals, impedances, regulator status and battery voltage. The processor 160' further includes the necessary communication links to other individual ASICs utilized within the IPG 100'. The processor 160', like all similar processors, operates in accordance with a program that is stored within its memory circuits.

The analog IC (AIC) 190' may comprise an ASIC that functions as the main integrated circuit that performs several tasks necessary for the functionality of the IPG 100', including providing power regulation, stimulus output, and impedance measurement and monitoring. Electronic circuitry 194' performs the impedance measurement and monitoring function.

The analog IC 190' may also include output current DAC circuitry 186' configured to supply current to a load, such as tissue, for example. The output current DAC circuitry 186' may be configured to deliver up to 20 mA aggregate and up to 12.7 mA on a single channel in 0.1 mA steps. However, it will be noted that the output current DAC circuitry 186' may be configured to deliver any amount of aggregate current and any amount of current on a single channel, according to one exemplary embodiment.

Regulators for the IPG 100' supply the processor and the digital sequencer with a voltage. Digital interface circuits residing on the analog IC 190' are similarly supplied with a voltage. A programmable regulator supplies the operating voltage for the output current DAC circuitry 186'. The coupling capacitors $C_X$ and electrodes $E_X$, as well as the remaining circuitry on the analog IC 186', may all be housed within the hermetically sealed case of the IPG 100. A feedthrough pin, which is included as part of the header connector 192', allows electrical connection to be made between each of the coupling capacitors $C_N$ and the respective electrodes $E_1, E_2, E_3, \ldots$ or $E_{16}$.

The digital IC (DigIC) 191' functions as the primary interface between the processor 160' and the output current DAC circuitry 186', and its main function is to provide stimulus information to the output current DAC circuitry 186'. The DigIC 191' thus controls and changes the stimulus levels and sequences when prompted by the processor 160'. In an exemplary embodiment, the DigIC 191' comprises a digital application specific integrated circuit (digital ASIC).

With the basic structure of an implantable stimulator understood, focus now shifts to a detailed description of the electrode selection techniques that are the focus of this disclosure.

The present invention employs objective and subjective measurements used in conjunction with an intelligent algorithm to find a subset of electrodes on the IPG 100 which may be evaluated in a clinical programming session. Objective neurophysiological and electrostimulation measurements are obtained first, followed by subjective psycho-physical measurements to identify a subset of electrodes most likely to result in an optimal therapeutic patient outcome.

In spinal cord stimulation, factors that determine the efficacy of the therapy are the electrode 106 geometry on the array 110, the distance (dCSF) of the electrodes 106 from the dorsal surface of the spinal cord, the relative orientation of the electrodes 106 to the physiological midline of the spinal cord, and the dorsoventral position of the stimulating electrodes 106 in the epidural space 70. Of these variables, only the design and configuration of the electrode array 110 are predetermined in advance. Once the specific type of electrode array 110 is selected, e.g., an in-line percutaneous array having electrodes placed in a straight line or a paddle-type of lead having electrodes spaced over a flat paddle surface, the electrodes to be activated and the specific stimulation parameters at those active electrodes (pulse width, amplitude, and frequency) may be determined by the clinician.

Figure 8:
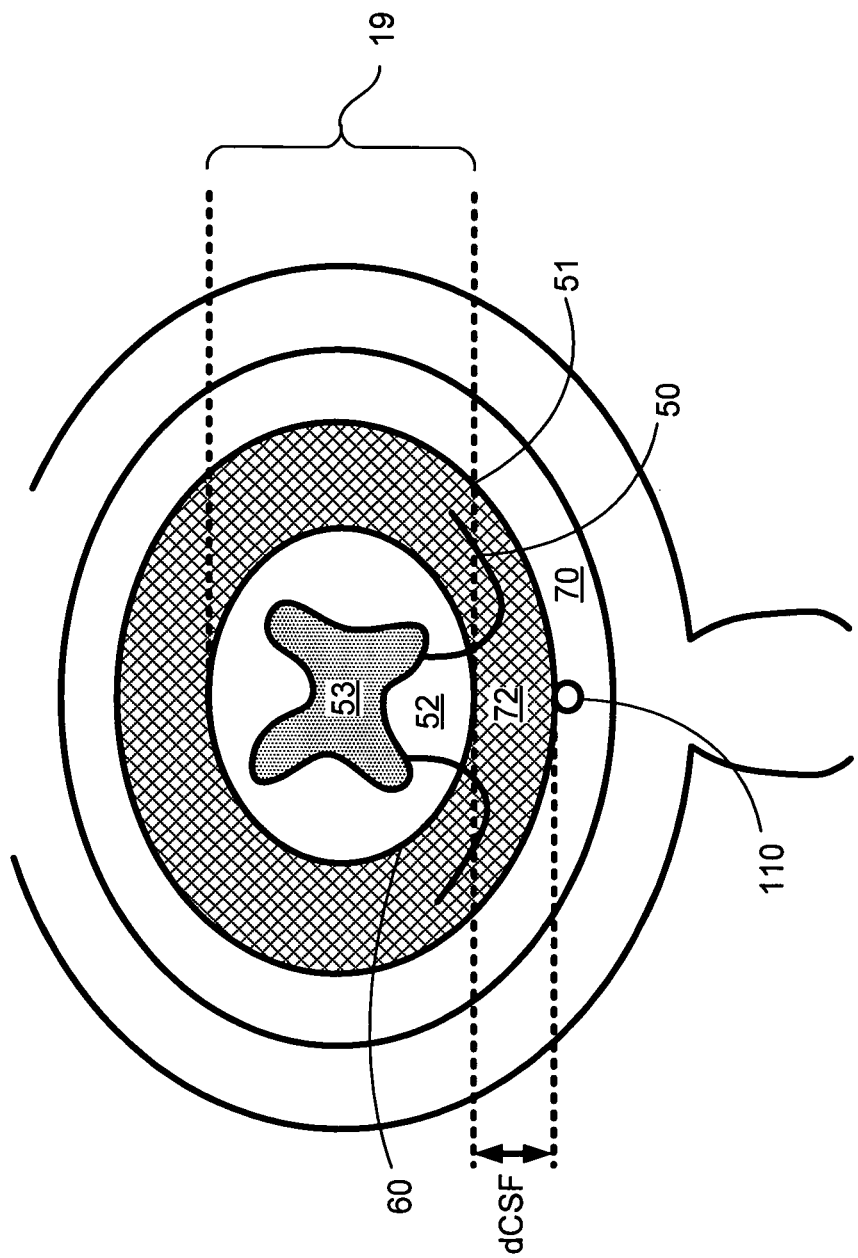
FIG. 8 shows a cross-sectional, transverse diagram of a spinal cord segment and parallel placement of an in-line electrode array at the midline.

It is instructive to understand an exemplary stimulation system that may employ the method of the present invention. FIG. 8 shows a cross-sectional, transverse view of a spinal cord segment showing placement of an exemplary in-line electrode array 110 parallel with the spinal cord 19 and near the physiological mid-line. The electrode array 110 is placed directly on the dura mater 51 within the epidural space 70. Cerebro-spinal fluid 72 is between the electrode array 110 and the white matter 52 of the spinal cord 19. Dorsal root nerves 50 and 60 are shown emanating from grey matter 53. dCSF is the distance or thickness of the cerebro-spinal fluid 72 that is interposed between the electrode array 110 and the dorsal surface of the spinal cord white matter 52.

Figure 9:
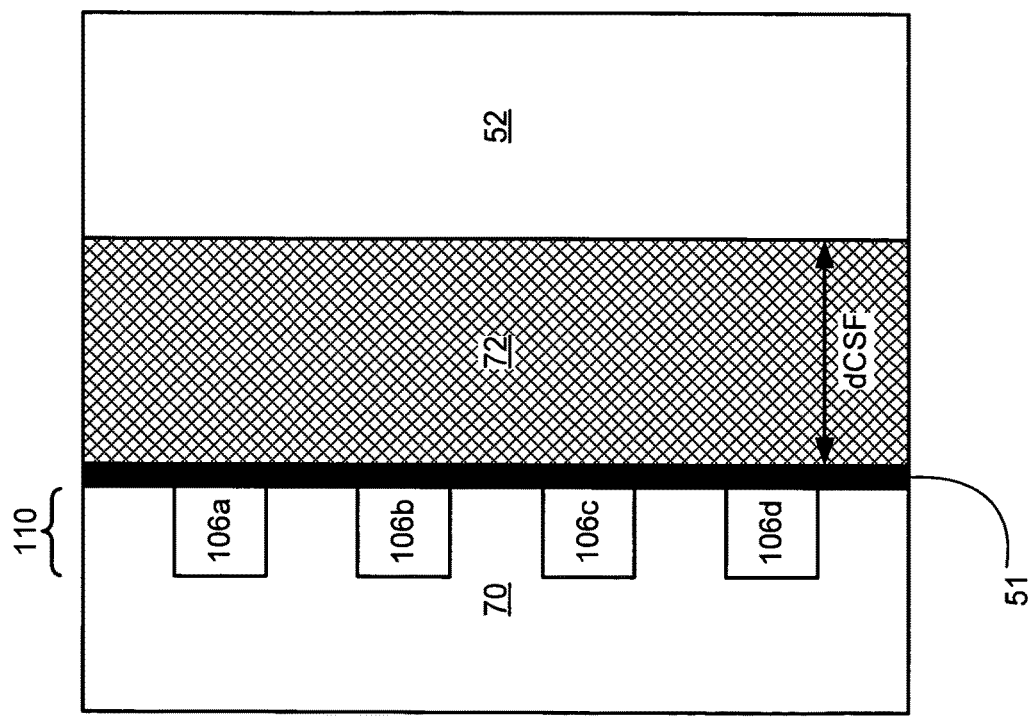
FIG. 9 shows a cross-sectional, midsagittal view of an in-line electrode array with the array placed at the physiological midline.

FIG. 9 shows a side, vertical cross-sectional, midsagittal representation of a spinal cord and an exemplary in-line electrode array placed relative to physiological mid-line. As shown, electrodes 106a, 106b, 106c, and 106d are placed in close proximity to the dura matter 51 in the epidural space 70. The electrodes 106a-d are electrically connected to IPG 100 which, as noted above, generates a stimulus pulse and measures potentials on electrodes 106a-d. While the body 108 (FIG. 3A) of the lead is not shown in FIG. 9, it is to be understood that the electrodes 106a-d are carried on the lead body, and that the lead body is simply not shown for convenience. Moreover, a typical IPG 100 may usually have a plurality of electrodes, e.g., eight or sixteen or more. The depiction of four electrodes 106a-d in FIG. 9 should therefore only be understood as illustrative and not limiting.

To stimulate the nerve, a supra-threshold stimulation pulse may be produced from IPG 100 and applied to electrodes in many different combinations. For example, a selected pair of the electrodes, e.g., electrodes 106a and 106b can be used in a bipolar mode, in which one electrode comprises an anode or source of current while the other comprises the cathode or sink of current. Or, the electrodes can be activated in a multipolar mode, e.g., with electrodes 106a and 106b comprising anodes and electrode 106c comprising a cathode. Likewise, the electrode can be activated in a monopolar mode, in which one electrode is active and the case 116 (FIG. 3) of the IPG 100 comprises the return electrode. Referring to FIG. 9, and to illustrate a bipolar mode of operation, current can be sourced from an electrode (e.g., 106a), through the dura mater 51, into the cerebrospinal fluid 72 to the white matter 52, and return (sink) to another electrode (e.g., 106d).

Any of the electrodes 106a-d may be used in a sensing or recording mode as well as a stimulating mode. To measure dCSF, i.e., the distance between the dura 51 and spinal cord white matter 52, at least two of the electrodes are used to complete a current delivering circuit, e.g., 106a as the anode (source) and 106d as the cathode (sink). At least one other electrode is used to sense the voltage (field potential) produced by the sourced current, for example, at electrodes 106b and/or 106c. The field potential sensed by these sensing electrodes may be made with respect to any other electrode(s) (e.g., the potential sensed between 106b and 106c) or to any other sensible potential (e.g., from 106b and/or 106c to ground, to the IPG case, etc.). In any event, when current is forced to flow between electrodes 106a and 106d, a variable field potential is developed at locations between these two electrodes at the location of the sensing electrode(s) 106b and/or 106c. White matter 52 and grey matter 53 have higher resistivity than does cerebro-spinal fluid 72, which is highly conductive. As white matter 52 comes closer to the sensing electrode(s), the field potential lines will necessarily become compressed, forcing more current to flow in a smaller thickness of cerebrospinal fluid, dCSF. This compression of field potential lines will cause the field potential measured at sensing electrode(s) 106b and/or 106c to change perceptibly such that the potential difference between these electrodes increases. In other words, perturbation in the measured field potential can be used to estimate the distance, dCSF.

While the sensing electrodes may normally be between the two or more stimulating electrodes, this is not strictly required. For example, and still referring to FIG. 9, current may be provided by electrodes 106a and 106b with field-potential sensing occurring at electrode(s) 106c and/or 106d. Such an alternative can have a more proximal sensitivity than the current source/sink pair (106a and 106d) and sensing pair (106b and 106c) discussed above.

In another alternative, the case or housing 116 of the IPG 100 (FIG. 3A) may be used as a return, indifferent electrode. In such an instance, at least one electrode (e.g., 106a) may function as a stimulating cathode, with at least one electrode (e.g., 106b) functioning as the sensing electrode. As the electrode array 110 is pushed against the dura matter 51, dCSF decreases, forcing more current to flow past the sensing electrode 106b and causing the field potential sensed at that electrode to increase.

Such techniques for measuring field potentials, and the use of such a measurement to estimate dCSF, is disclosed in Publication No. IPCOM000021845D, published at www.ip.com on Feb. 12, 2004, which is submitted herewith and is incorporated herein by reference in its entirety. The estimated dCSF may then be stored in memory in the IPG 100 for later reference, so that the next time a dCSF measurement is made, a determination can be made as to whether the dCSF has changed, and if so, by how much and what the rate of change is.

It is emphasized that the electrodes 106a-d may be dedicated exclusively to either stimulation or sensing and, in some instances, may function as both, in a time-multiplexed manner. Preferably, each electrode 106 in the IPG 100 can operate as either a stimulating or sensing electrode, with the mode being determined by switches capable of connecting the electrode to current generation circuitry or voltage sensing circuitry.

The method of the present invention uses objective measurements on each electrode to determine which seem likely pursuant to a given objective measurement to be most beneficial in a given patient's therapy. Additionally, subjective measures for each electrode based on the patient's feedback are preferably (but not necessarily) used to quantify the efficacy of a particular electrode. When these objective and possibly subjective measurements are taken on the patient for each electrode, the results of the measurement is assessed, and ultimately the measurements on each electrode are weighted so that presumably more significant measurements are given larger influence. In the end, these weighted measurements for each electrode are summed to provide a total weighted effect of the various measurements per each electrode. With this information, a subset of electrodes can be chosen which are presumed to be logically efficacious for a given patient, and the clinician may then attempt to set the optimal stimulation parameters (e.g., pulse width, amplitude, and frequency) via experimentation with just the chosen subset of electrodes.

This approach to choosing electrodes for further clinical scrutiny can be expressed mathematically as determining a value for each electrode that comprises a weighted sum of the "i" measurements taken with respect to each electrode, where:

$$\text{Value}(E_X) = \sum_i W_i * M_{i,X}$$

where, $W_i$ equals a weight to be attributed to the i-th measurement, and $M_{i,X}$ equals the value of the ith measurement taken at the X-th electrode. Once these values are attained for each electrode (Value($E_X$)), it will become apparent that some of the X electrodes are more suitable for activation in the provision of therapy to a given patient. Hence, a subset of electrodes can be ascertained from among the X electrodes for activation and analysis by the clinician. By reducing the number of active electrodes, the clinician efforts in determining optimal stimulation parameters for the patient is more focused, and more likely to achieve better results in a faster amount of time.

Figure 11:
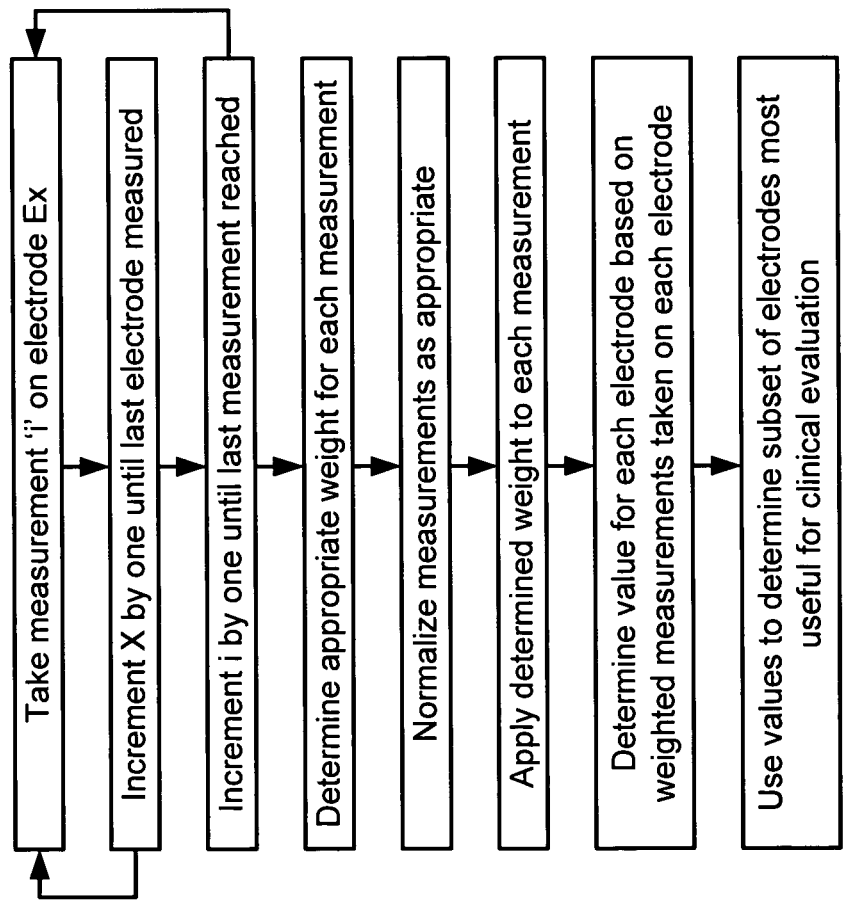
FIG. 11 shows, in accordance with the present invention, a block flow diagram of one embodiment of the method illustrated in FIGS. 10A-10C for arriving at a subset of electrodes in an implanted stimulator device.

There are many ways to implement such an algorithm for electrode activation optimization, and one example is shown by example in FIGS. 10A-10C, which is summarized in flow chart form in FIG. 11. One skilled in the art will appreciate that the disclosed method, essentially amounting to a measurement and optimization algorithm, can be performed automatically by any of several components in the IPG system, e.g., within the microcontroller 160 of the IPG 100 itself (FIG. 5), within the HHP 202 or CP 204 via telemetry of data, etc.

FIG. 10A shows various per-electrode measurements that are taken, for example, by a clinician, after an IPG 100 has been implanted into a patient. In this example, 'i' measurements are taken, three of which are objective and one of which is subjective. However, it is important to note at this point that the invention can also be used wholly with objective measurements or wholly with subjective measurements. Hence, the illustration of a mixture of objective and subjective measurements should be understood as merely illustrative.

The first electrode measurement is electrode impedance. In a preferred embodiment, such impedance is measured by running a constant current through a given electrode, and measuring the resulting voltage on that electrode while holding the IPG 100 case 116 (FIG. 3A) to ground as a reference potential. That is, the impedance measurement is preferably performed on each electrode as a monopolar measurement, although this is not strictly required, as other reference potentials could be used as well. In any event, the constant current is preferably a subthreshold current that will not invoke a perceptible response in the possible stimulation of the patient's tissue. With this current sourced (or sunk) from a given electrode, the measured voltage while delivering the current at the node is divided by the constant current to arrive at the impedance via Ohm's law. Alternatively, the impedance measurement can comprise an application of a constant voltage at each electrode, followed by monitoring of the resulting current, which again are divided to ascertain the impedance.

The impedance at each electrode comprises a particularly useful value in the scheme of the overall method, as it tends to highlight electrodes that for one reason or another are likely not sensible to activate, either because they electrodes are short circuited or open circuited. For example, in FIG. 10A, it is seen that the impedances are comparatively high electrodes $E_1$ and $E_2$, and is very high (essentially an open circuit) for electrode $E_8$. This suggests that these electrodes, for some reason are not making good ohmic contact with the tissue. As a result, provision of therapeutic currents through these electrodes might require unacceptably high voltages that the IPG 100 would be unable to produce. In other words, it would be generally unfavored to choose electrode $E_1$, $E_2$ or $E_8$ in the subset of suitable therapeutic electrodes, and as will be seen, the disclosed method indeed arrives at this result, although taking other factors into account.

Although shown in FIG. 10A as actual resistance values, one skilled will recognize that other values could be used as proxies for the actual impedance. For example, if the compliance voltage is used to output the constant current (e.g., 0.3 mA), its value will be related to resistance, and so such voltage values could be used as well. The same can be said for the other measured values illustrated in FIG. 10A, and thus it should therefore be understood that such measured values are merely exemplary.

As noted above, open circuits and short circuits are concerns at the electrodes, and either condition can render an electrode not suitable for inclusion in the subset of potential electrodes for activation by the clinical in later testing. However, should a given electrode be shorted, application of the disclosed method might inadvertently consider such an electrode as particularly good, when in fact this is not the case. Therefore, it may be sensible to set the measured value for shorted electrodes (e.g., those with impedances less than 50 ohms) to a high value (e.g., 10 kOhm) to put them on numerical parity with other "bad" electrodes which the disclosed technique seeks to identify.

The next objective measurement in FIG. 10A taken for each electrode is the field potential. Because the measuring of field potentials in the context of determining dCSF was explained earlier, the same is not reiterated here. Because the thickness of the cerebro-spinal fluid, dCSF, is related to the measured field potential, that derived value could also be used as a per-electrode measurement used in FIG. 10A.

As shown in FIG. 10A, notice that the field potential measurement entry has been inverted (i.e., 1/the field potential). This is because in the disclosed embodiment, lower values for the per-electrode measurement indicate a more likely electrode candidate to be chosen for activation. Because higher field potential voltages correspond to a smaller dCSF, which in turn correspondence to easier stimulation, the field potential voltage is inverted such that smaller inverted values indicate electrodes that are closest to the spinal column, and preferably chosen for activation. However, it should be realized that the charted entries for each of the illustrated measurements need only correspond generally to an electrode capacity to be more or less useful in a given patient's therapy. Again, the actual value used in FIG. 10A can therefore be somewhat arbitrary. As shown, the measured field potential values tend to exhibit more favorable responses (i.e., lower values) for those electrodes nearer to the middle of the lead, which can make sense given the lower impedances generally seen at those electrodes via the first objective measurement.

The third objective measurement shown in FIG. 10A corresponds to a given electrode's ability to actually provoke a perceptible nerve response. In a preferred embodiment, this is preferred by providing a constant current at a given electrode ($E_X$), and measuring the response at an adjacent electrode ($E_{X+}$ and/or $E_{X-}$). Such a response is generally referred to as an evoked action potential, and one skilled in the art understand that means for measuring such evoked action potentials are known in the art; hence the specifics of this measurement is not further discussed, although exemplary patents disclosing techniques for sensing action potentials include U.S. Pat. Nos. 5,702,429; 5,814,092; and 5,913,882, which are all incorporated herein by reference in their entireties. Briefly, the nerve response can be measured with a high-gain amplifier connected to the sensing electrodes. The morphology of the nerve response may be acquired and analyzed by a software program to confirm that it is a nerve fiber of interest.

In a preferred embodiment, the measurement reflected in FIG. 10A comprises the constant current value at which a nerve response was detected at the adjacent electrode, i.e., what amounts to an estimation of the threshold stimulation current. Hence, for this measurement, at each electrode, a constant current is gradually increased in stair-step fashion until this current threshold is detected, which then becomes the measured entry in the table. In the example shown, those electrodes in the middle of the lead generally more easily are able to evoke a nerve response, as reflected by the lower current values at which nerve response was detected. This makes sense in light of the other objective measurement already taken—impedance and field potential—which too tended to favor the middle electrodes as most suitable for efficiently inducing a therapeutic response. Alternatively, the measured amplitude of the evoked nerve action potential could be used as the measurement. In this case, a larger amplitude might indicate better proximity to the dorsal columns and thus these would be better electrodes to include in the electrode subset for subsequent clinical testing with the patient.

The last exemplary measurement shown in FIG. 10A is subjective, and essentially amounts to quantification of user feedback to various stimuli at the electrodes, what can be referred to as psychophysical measurements. Essentially, this measurement (referred to as a "measurement" herein for simplicity despite lack of automated sensing by the IPG 100) seeks to quantify the patient's perception in response to stimulation at each electrode. Because of the subjective nature of this measurement, which is optional and not required in all embodiments of the invention, the patient or clinician must populate the chart of FIG. 10a, e.g., by telemetering the inputs for each electrode back to the IPG 100 for storage with the other objective measurements. Logically, the objective measurements would be performed first as they may be performed automatically and more quickly than psychophysical measurements which require comparatively time-consuming patient feedback.

As with the objective measurements discussed above, there are many different ways in which a patient or clinician could choose to quantify a given patient's response. In one example, a constant current of a given nominal value (e.g., 3 mA) could be provided in monopolar fashion at each electrode, with the patient asked to quantify the nature of what he or she is feeling. No sensation, or a painful or uncomfortable sensation, could be rated highly, for example, on a scale from 1 to 10, which would indicate that the electrode in question. Other sensations over and beyond the general tingling sensation of paresthesia that the IPG seeks to promote, could be given relative high values (e.g., 5 or 6). Pleasurable sensations, such as those effective to mask the patient's pain without producing unwanted or unusual sensations, could be given a relatively low number (e.g., 1-4).

In another example, the measured value can be that at which the patient experiences some sensation, such as pain or muscle cramping. The constant current at which this effect occurs can be the per-electrode measured value for the purpose of the chart of FIG. 10A.

Once the various per-electrode measurements have been taken, the disclosed algorithm analyzes the data to determine which of the various measurements reflect differences in the electrodes, and hence highlight which measurements should be most considered in determining a subset of electrode for activation in determining more specific stimulation parameters for a patient's therapy. For example, consider if a given measurement (e.g., impedance) showed no or minimal variation between the various electrodes. In that case, the impedance measurement would do little to inform the clinician which electrodes to focus on first in setting up a patient's therapy. By contrast, what if one set of measurement favors selection in the subset of a particular number of electrodes, while another measurement favors selection of different electrodes? Such lack of information, or conflicting information, could be confusing to the clinician, and would do little to inform the clinician about electrodes to which focus should be directed.

The disclosed scheme addresses these issues by taking multiple measurements (at least two, whether they be subjective or objective), and weighting those measurements depending on their variation, with higher variation measurements being given more weight. There are many different ways in which this can be done, but one way is shown in progressive steps in FIGS. 10A through 10C. As shown in FIG. 10A, once the various measurements are taken, their standard deviation and averages are taken, and are divided. This ratio, known as the coefficient of variation, provides a normalized metric for how varied measurements are around the given measurement's average. Therefore, in FIG. 10A, it is not surprising that the STD/AVG ratio for the impedance measurement is high compared to the nerve response ratio, because the impedance varies by orders of magnitude whereas the nerve response does not. In recognition of the potentially naturally larger variance between the different measurements, it may make sense for some of the measurements to be logarithmically or exponentially scaled to bring their variance into line with the variances of other measurements. However, this is not shown in FIG. 10A for convenience.

By reviewing the STD/AVG ratio, we see the largest normalized per-electrode variation in the impedance measurement, followed by user input, nerve response, and field potential measurements, and they are so ranked in order of their variance. This generic variance ratio can in a simple embodiment be used to set the weighting value of the measurements. For example, it may be the case that a user simply wants to assign the highest-ranking measurement as having a 40% weight, the next highest as a 30% weight, the next as a 20% weight, and the lowest as a 10% weight, assuming that there are four measurements. Alternatively, the weighting can be a function of the STD/AVG ratio itself, with each measurement being weighted in accordance with the relative magnitude of the ratio. For example, the impedance measurement could be weighted as 0.99/(0.99+0.13+0.33+0.39)=53.8%, etc. In short, the weight accorded to any given measurement, like many other aspects of the disclosed technique, can be somewhat arbitrary and subject to a user's particular desires, perhaps as informed by experimentation.

However, the weight for the various measurements can also be determined empirically, or from the clinician's experience. For example, impedance measurements are known to be variable and affected by anatomic and physiological factors that are not clinically important. For this reason, the impedance measurement may simply be weighted by no more than 20% as a matter of course, regardless of its variability, standard deviation, etc. By contrast, because nerve response actually measures a physiological response to stimulation, it may be given more weight as a matter of course, for example 30%. However, because the correlation of nerve response to clinical success may vary dramatically from patient to patient, it may make sense to give the user input measurements the highest predictive weight, for example, 50% as a matter of course, because these measurements relate most directly to patient satisfaction with the therapy. In other words, the weighting of the various measurements can be mathematically determined on the basis of the measurements, or may be predetermined.

While it has been disclosed in FIG. 10A that a measurement with high variability is an interesting or significant measurement deserving of high weight in the overall per-electrode value calculation, it should also be noted that high variability may suggest the contrary. For example, if it is determined that there is too much noise or electrode polarization effects as concern the nerve response measurement, it may simply be the case that the nerve response measurement is simply unreliable in choosing optimal electrodes. By contrast, if it is observed that the impedance measurements have a low variation (e.g., standard deviation), the impedance measurements could be given more weight than the nerve response measurements in choosing electrodes of interest. In short, what is important is intelligent weighting of the measured values such as appears in FIG. 10A. The criteria for weighting those measurements can vary given an appropriate understanding of the physics involved and empirical experience with the various measurements.

Regardless, once the weights are determined for the various measurements, these weights are applied to the per-electrode measurements to yield a final value for each electrode, Value($E_x$). To make this value more meaningful, it can be useful to normalize the results of the measurements, such as is reflect in FIG. 10B, in which each measurement has been divided by that measurements average value. Such normalization of the measurements tends to bring the measured numbers into closer parity with each other, and makes the overall effect of each measurement on the final value more meaningful. However, it is worth noting that measurement normalization, while preferred depending on the nature of the measurements, is not required in all useful embodiments.

Once the measurements are normalized, they can be multiplied by the earlier-determined weights for each, and then summed, as shown in FIG. 10C. This summed value, Value($E_x$), thus represents a single relative value which indicates, on the basis of the previous measurements, which electrodes are the mostly likely logical candidates for consideration by the clinician in determining optimal therapy for the patient. In the example of FIG. 10, note that smaller measured values for each measurement were indicative of more favorable electrodes for consideration. (For some measurement such as field potential, this was achieved by inverting the measurement). Thus, when weighted and summed, the electrodes with the lowest summed values for Value($E_x$) are those mostly likely to achieve a good therapeutic response, or to achieve such a response efficiently and respectfully of the limited power of the IPG 100. In the example shown, note that the middle electrodes $E_3$-$E_6$ had the lowest values. Therefore, if we assume the goal is to define the subset of activatable electrodes as half of the possible electrodes (other criteria are of course possible), then these four electrodes can become the exclusive focus of the clinician in determining optimal patient therapy.

At this point, and as noted above, the IPG 100 is ready to be optimized, and part of this procedure is to choose the electrodes that are most sensible to activate as part of the patient's therapy. As noted earlier, it is not immediately obvious which of the various electrodes might be most suitable for activation, and in part, this is why an array of electrodes is used, i.e., so that those having the best effect can be chosen for activation, while other electrodes simply might never be used at all. In any event, the method of the present invention for determining optimal electrodes should greatly facilitate the clinician by limiting the number of possible therapy options to be tried on a given patient. With the smaller number of electrodes left in the subset, it is now exponentially easier to determine in a clinical setting the patient's optimal stimulation parameters (e.g., pulse width, amplitude, and frequency) and the electrodes to provide those parameters.

The objective and subjective measurements may be performed with the patient in several different postural position(s). If such an alternative method is used, these various postural measurements for each electrode can themselves be weighted for each electrode before consideration of the weighting of the various measurements. For example, if a patient is expected to sit for 60% of the duration of stimulator use, stand for 20%, and lie down for 20%, the measurements for these various postures can be weighted accordingly before application of the disclosed method.

Additionally, the interpretation of the measurements, and how they are weighted, may be improved by use of comparative norms obtained from a database. A database containing similar information from previous tests of implanted patients, from published literature, and/or experimental sources may be attached to the computer system/programmer that implements the method. For example, the database may provide information regarding the typical values of field potentials for various actual dCSF levels. This might be used to provide much better estimates of the dCSF for measurements made on the presently tested patient. In addition to measurement distributions, the database may also contain information as to the vertebral location and mediolateral placement of the lead, from standard medical imaging sources such as fluoroscopy, computerized tomography, MRI, etc. This information may be from the present patient, as well as from past patients. Again, this information may be used to both improve the interpretation of and used in conjunction with the objective and subjective measurements to reduce the number of testable electrodes.

Although it is preferred to sum the weighted measurements to arrive at the value for each electrode (Value($E_X$)), the value can also be arrived at differently, for example, by averaging the measurements instead of summing them. In short, there are many different logical ways to arrive at a value for each of the electrodes, and disclosure of a weighted sum should not be understood as limiting.

Although the disclosed technique can been disclosed as reducing the number of possible electrodes for clinical analysis to a subset, it should be realized that the method can also be used to positively determine the electrodes to be used for a given patient without the need for further clinical evaluation. For example, and referring again to FIG. 10C, it is seen that electrodes E3 and E5 render the lowest (in this example, best) electrode values. Armed merely with this knowledge, the clinician may assume that these two comprise the best two electrodes, and further clinical evaluation can proceed accordingly. For example, the clinician may need to merely set electrode E3 as the anode (source) and E5 as the cathode (sink), and proceed to clinically determine with patient feedback the optimal stimulation parameters (e.g., pulse width, amplitude, and frequency). In other words, the determined subset may merely set the electrodes to be used, without the needs to further reduce this subset via clinical testing.

It should be understood that reference to an "electrode" implantable adjacent to a tissue to be stimulated includes electrodes on the implantable stimulator device, or associated electrode leads, or any other structure for directly or indirectly stimulating tissue.

While the invention herein disclosed has been described by means of specific embodiments and applications thereof, numerous modifications and variations could be made thereto by those skilled in the art without departing from the literal and equivalent scope of the invention set forth in the claims.

What is claimed is:

1. A method of using a plurality of electrodes of a stimulator device implanted in a patient, the method comprising:
    providing a stimulator device comprising a plurality of electrodes, wherein the stimulator device is implanted in a patient;
    taking a first type of measurement for each of the plurality of electrodes of the stimulator device;
    taking a second different type of measurement for each of the plurality of electrodes of the stimulator device, wherein the measurements are indicative of the ability of the respective electrode if activated to provide useful therapy to the patient in which the stimulator device is implanted;
    applying a first weight to the first type of measurement to respectively arrive at first weighted measurements for the respective electrodes;
    applying a second weight to the second type of measurement to respectively arrive at second weighted measurements for the respective electrodes;
    computing a function of the first and second weighted measurements to arrive at a value;
    using the value to determine a subset of the electrodes; and
    activating at least one electrode of the subset of the electrodes to deliver therapy to the patient.

2. The method of claim 1, wherein at least one of the first and second types of measurement is selected from the group consisting of electrode impedance, field potential, and nerve response.

3. The method of claim 2, wherein one of the first and second types of measurement is a quantitative value indicative of subjective user feedback based on stimulation of a given electrode.

4. The method of claim 1, wherein the first type of measurement is one of an electrode impedance, a field potential, a nerve response, and a qualitative value indicative of subjective user feedback based on stimulation of a given electrode, and the second type of measurement is another different one of the electrode impedance, the field potential, the nerve response, and the qualitative value indicative of subjective user feedback based on stimulation of a given electrode.

5. The method of claim 1, wherein the first type of measurement is objective and the second type of measurement is subjective.

6. The method of claim 1, wherein the function comprises summing the first and second weighted measurements for each electrode.

7. The method of claim 1, wherein one of the first and second types of measurement is indicative of a thickness of a cerebro-spinal fluid.

8. The method of claim 1, wherein at least one of the first and second types of measurement is normalized before applying at least one of the first and second weights to the at least one first and second types of measurement.

9. The method of claim 1, further comprising determining at least one of the first and second weights for at least one of the respective first and second types of measurement by an assessment of a variance of the respective measurements between the plurality of electrodes.

10. The method of claim 1, wherein at least one of the first and second weights is predetermined.

11. The method of claim 1, wherein the first type of measurement is considered more significant and the first weight is applied to the first type of measurement, such that the first type of measurement is given a larger influence on the value.

12. A method of using a plurality of electrodes of a stimulator device implanted in a patient, the method comprising:
    providing a stimulator device comprising a plurality of electrodes, wherein the stimulator device is implanted in a patient;
    taking a first type of measurement for each of the plurality of electrodes of the stimulator device;
    taking a second different type of measurement for each of the plurality of electrodes of the stimulator device;
    applying a first weight to the first type of measurement to arrive at first weighted measurements for the respective electrodes;
    applying a second weight to the second type of measurement to arrive at second weighted measurements for the respective electrodes;
    processing the first and second weighted measurements for each electrode to arrive at a value for each electrode;

using the values to determine a subset of the electrodes; and activating at least one electrode of the subset of the electrodes to deliver therapy to the patient.

13. The method of claim 12, wherein at least one of the first and second types of measurement is selected from the group consisting of electrode impedance, field potential, and nerve response.

14. The method of claim 13, wherein one of the first and second types of measurement is a quantitative value indicative of subjective user feedback based on stimulation of a given electrode.

15. The method of claim 12, wherein applying the first and second weights to the first and second types of measurement to arrive at the first and second weighted measurements for the respective electrodes comprises multiplying the weight for each measurement by the measurement for each electrode.

16. The method of claim 12, wherein one of the first and second types of measurement is indicative of a thickness of a cerebro-spinal fluid.

17. The method of claim 12, wherein at least one of the first and second types of measurement is normalized before applying at least one of the first and second weights to the at least one first and second types of measurement.

18. The method of claim 12, further comprising determining at least one of the first and second weights for at least one of the respective first and second types of measurement by an assessment of the variance of the respective measurements between the plurality of electrodes.

19. The method of claim 12, wherein at least one of the first and second weights is predetermined.

20. The method of claim 12, wherein processing the weighted measurements for each electrode comprises summing the first and second weighted measurements for each electrode.

21. The method of claim 12, wherein the first measurement type is objective and the second types of measurement is subjective.

22. The method of claim 12, wherein the first type of measurement is considered more significant and the first weight is applied to the first type of measurement, such that the first type of measurement is given a larger influence on the value.

* * * * *